US008945198B2

(12) United States Patent
Tegels et al.

(10) Patent No.: US 8,945,198 B2
(45) Date of Patent: Feb. 3, 2015

(54) LOCATING SIDE CATHETER BRANCH RELATIVE TO INFLATION PORTION

(75) Inventors: Zachary J. Tegels, Otsego, MN (US); Adam Jennings, Buffalo, MN (US); Tom Holman, Minneapolis, MN (US); Ben Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1238 days.

(21) Appl. No.: 12/183,894

(22) Filed: Jul. 31, 2008

(65) Prior Publication Data

US 2010/0030140 A1    Feb. 4, 2010

(51) Int. Cl.
| | |
|---|---|
| A61F 2/06 | (2013.01) |
| A61F 2/958 | (2013.01) |
| A61F 2/954 | (2013.01) |
| A61F 2/856 | (2013.01) |
| A61F 2/82 | (2013.01) |

(52) U.S. Cl.
CPC .............. *A61F 2/958* (2013.01); *A61F 2/954* (2013.01); *A61F 2/856* (2013.01); *A61F 2002/821* (2013.01)
USPC ........................................ 623/1.11; 623/1.35

(58) Field of Classification Search
USPC .............. 600/16, 30, 114, 143, 146, 152; 606/108, 153, 191; 623/1.11–1.12, 25, 623/1.35; 604/96.01
See application file for complete search history.

(56) References Cited

U.S. PATENT DOCUMENTS

| | | | |
|---|---|---|---|
| 4,983,167 A * | 1/1991 | Sahota | 606/194 |
| 6,210,429 B1 | 4/2001 | Vardi et al. | |
| 6,325,826 B1 | 12/2001 | Vardi et al. | |
| 6,520,988 B1 * | 2/2003 | Colombo et al. | 623/1.35 |
| 6,582,394 B1 * | 6/2003 | Reiss et al. | 604/96.01 |
| 6,692,483 B2 | 2/2004 | Vardi et al. | |
| 6,706,062 B2 | 3/2004 | Vardi et al. | |
| 6,709,440 B2 * | 3/2004 | Callol et al. | 606/108 |
| 7,220,275 B2 | 5/2007 | Davidson et al. | |
| 8,398,697 B2 * | 3/2013 | Holman et al. | 623/1.11 |
| 2004/0176837 A1 | 9/2004 | Atladottir et al. | |
| 2005/0102019 A1* | 5/2005 | Yadin | 623/1.11 |
| 2005/0154442 A1* | 7/2005 | Eidenschink et al. | 623/1.11 |
| 2006/0100694 A1 | 5/2006 | Globerman | |
| 2007/0100301 A1 | 5/2007 | Gumm | |
| 2007/0203562 A1 | 8/2007 | Malewicz et al. | |
| 2007/0208406 A1 | 9/2007 | Alkhatib et al. | |
| 2008/0033525 A1 | 2/2008 | Shaked et al. | |
| 2008/0086191 A1 | 4/2008 | Valencia et al. | |

FOREIGN PATENT DOCUMENTS

WO    2008054590    5/2008

* cited by examiner

*Primary Examiner* — Ashley Fishback
(74) *Attorney, Agent, or Firm* — Seager, Tufte & Wickhem LLC

(57) ABSTRACT

A side catheter branch of a catheter assembly is oriented with respect to the main or side balloons of a catheter assembly. In some examples, the orientation is accomplished by connecting the side catheter branch to the main and/or side balloons or waist portions thereof. In other examples, the side catheter branch is positioned within the folds of the main or side balloons during assembly of the catheter assembly. In this manner, the side catheter branch remains in a known orientation with respect to the main and/or side balloons prior to and/or after deployment.

17 Claims, 5 Drawing Sheets

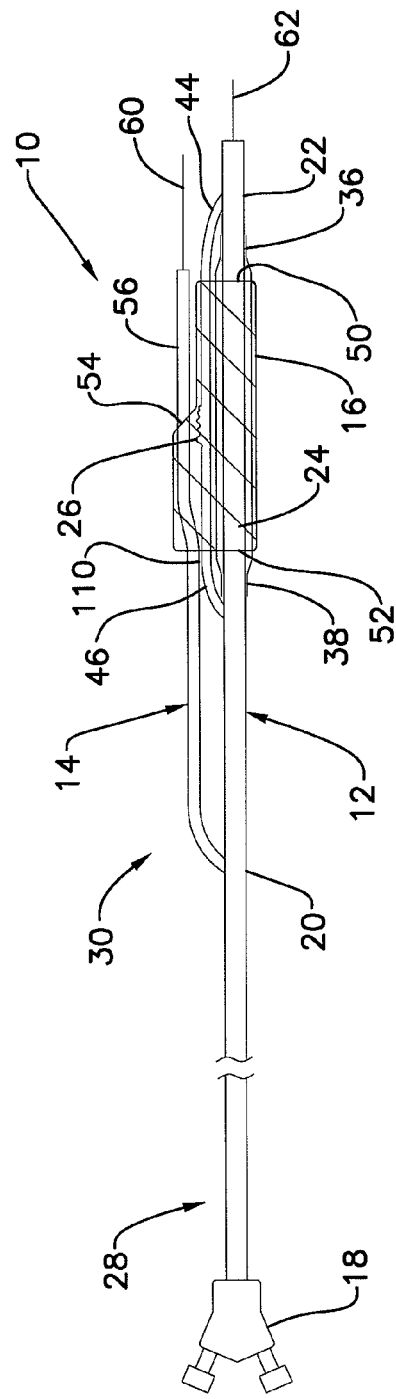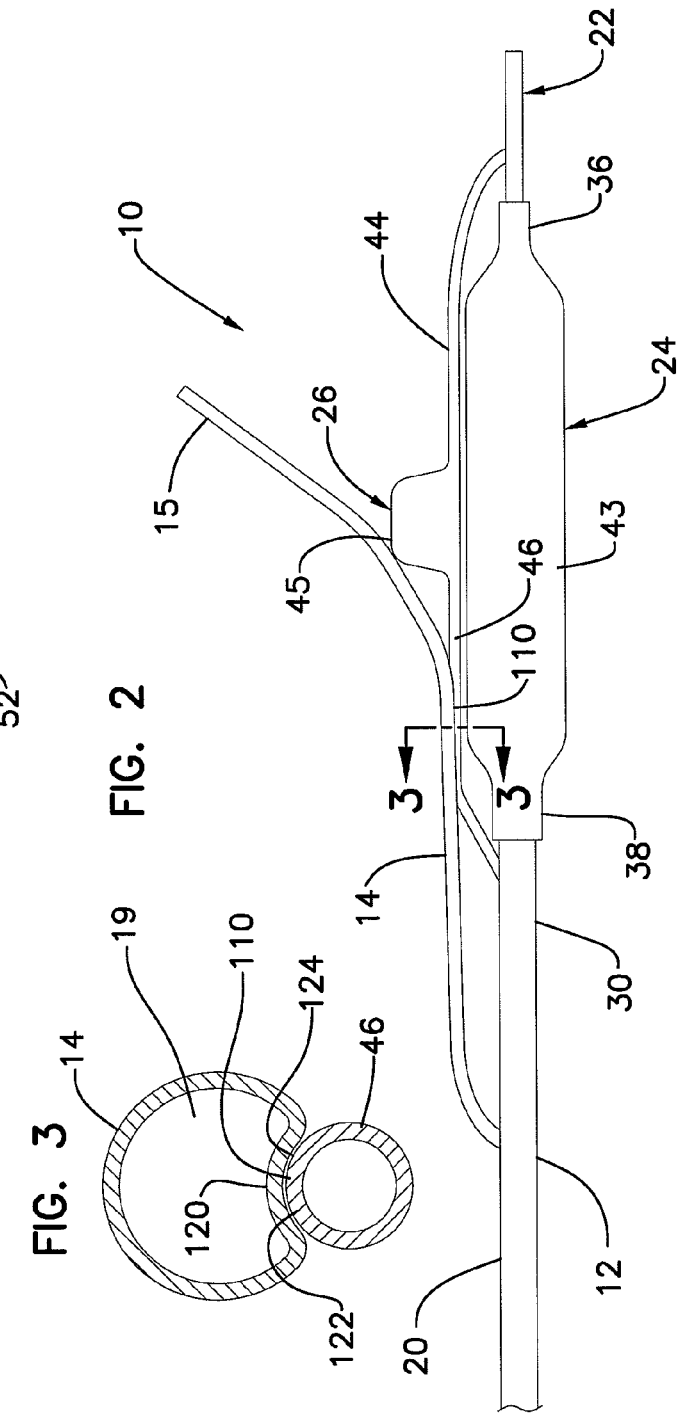

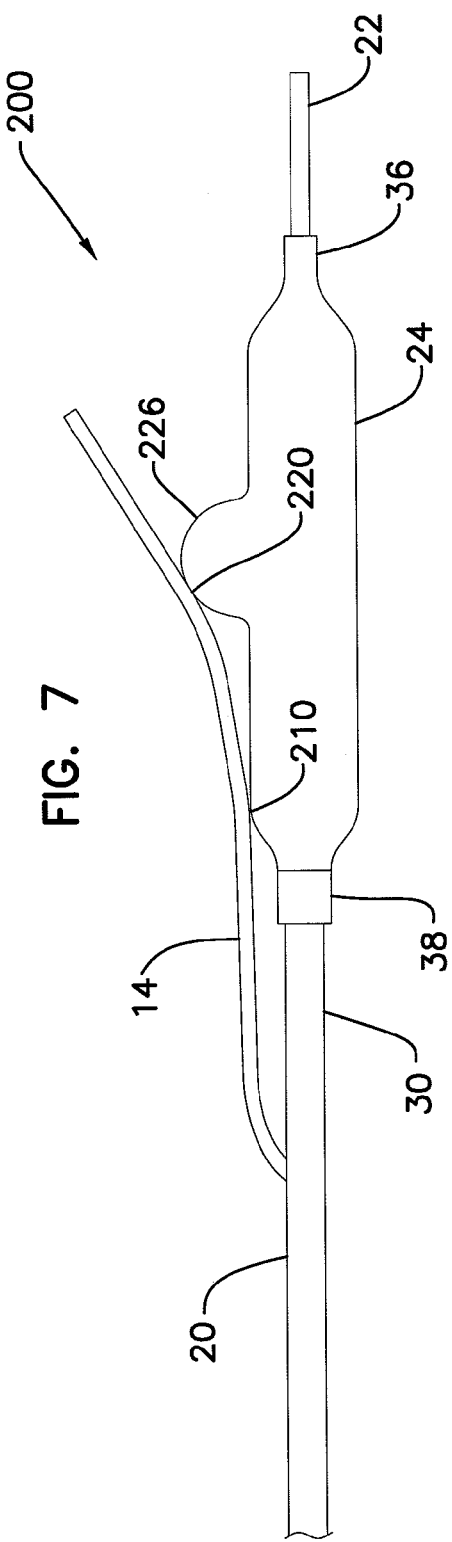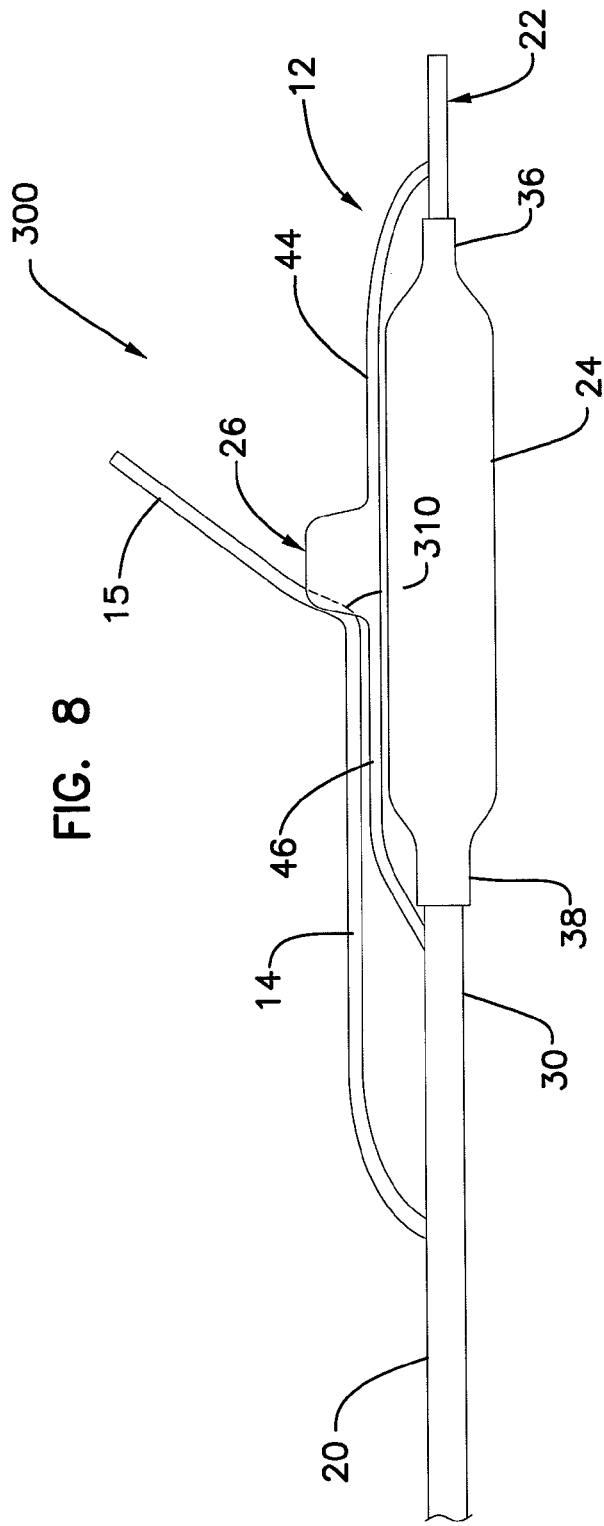

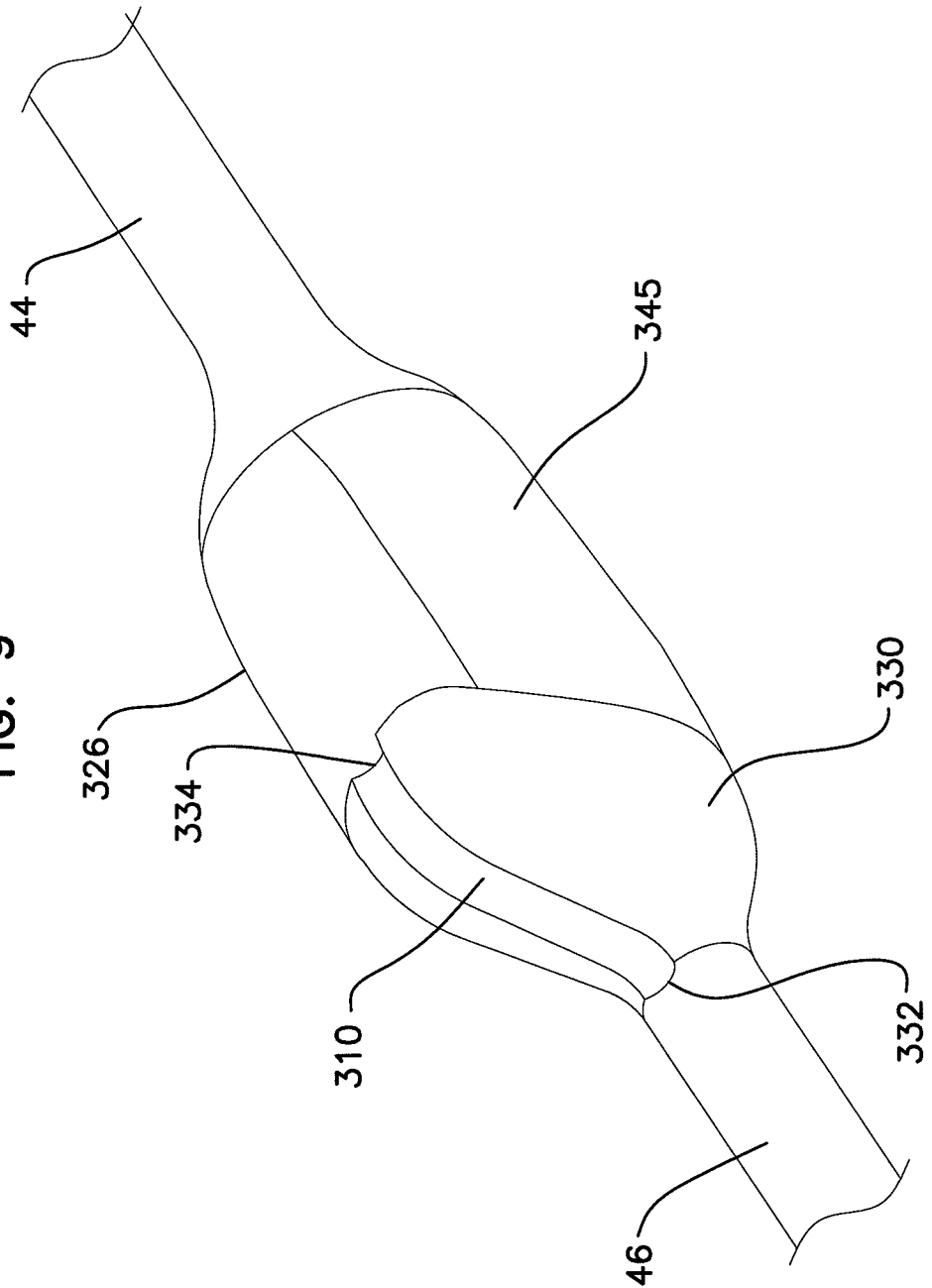

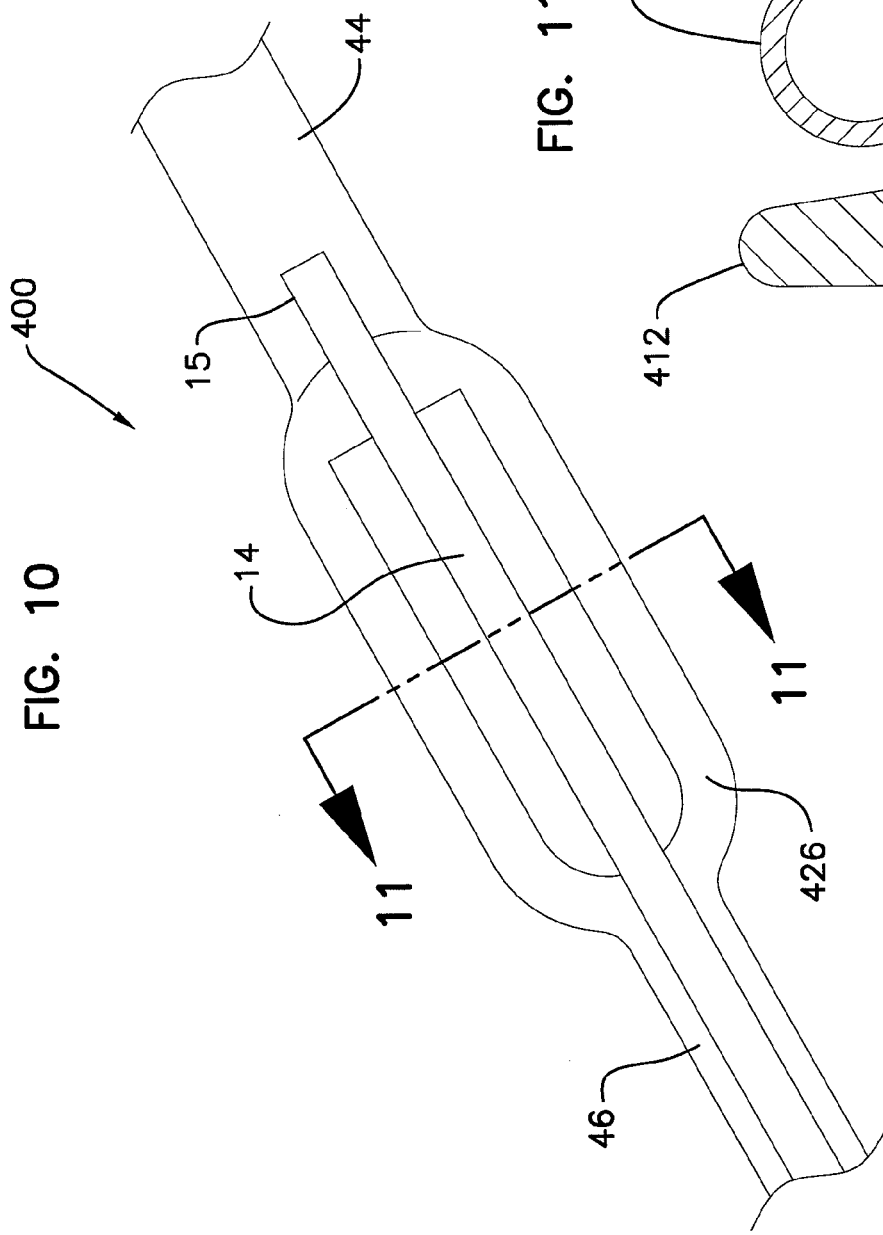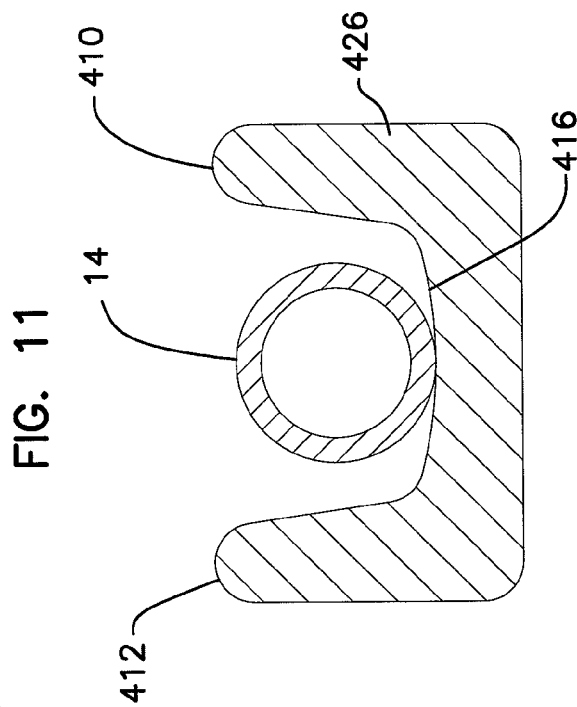

LOCATING SIDE CATHETER BRANCH RELATIVE TO INFLATION PORTION

TECHNICAL FIELD

This disclosure relates to catheter systems and methods for treating vessel bifurcations.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY

The present disclosure relates generally to catheter assemblies for treatment of bifurcated lumens in a patient, such as vessel bifurcations.

In one arrangement, a side catheter branch of a catheter assembly is oriented with respect to the main or side balloons of a catheter assembly. In some examples, the orientation is accomplished by connecting the side catheter branch to the main and/or side balloons or waist portions thereof. In other examples, the side catheter branch is positioned within the folds of the main or side balloons during assembly of the catheter assembly. In this manner, the side catheter branch remains in a known orientation with respect to the main and/or side balloons prior to and/or after deployment.

There is no requirement that an arrangement or method include all features characterized herein to obtain some advantage according to this disclosure.

DESCRIPTION OF THE DRAWINGS

FIG. 1 is a schematic representation of an example catheter assembly for treatment of a vessel bifurcation shown in a non-deployed state, the assembly constructed having a proximal end portion and distal end portion, wherein the distal end portion includes main and side balloons and main and side catheter branches.

FIG. 2 is a schematic representation of the catheter assembly of FIG. 1 shown in a deployed state and with the stent removed for clarity.

FIG. 3 is a cross-sectional view taken along line 3-3 of the side catheter branch and a waist of the side balloon of the catheter assembly of FIG. 2.

FIG. 7 is a schematic representation of another example catheter assembly for treatment of a vessel bifurcation shown in a deployed state and with the stent removed for clarity, the assembly constructed having a proximal end portion and distal end portion, wherein the distal end portion includes a main balloon and main and side catheter branches.

FIG. 8 is a schematic representation of another example catheter assembly for treatment of a vessel bifurcation shown in a deployed state and with the stent removed for clarity, the assembly constructed having a proximal end portion and distal end portion, wherein the distal end portion includes main and side balloons and main and side catheter branches.

FIG. 9 is a schematic perspective view of the side balloon of the catheter assembly of FIG. 8.

FIG. 10 is a schematic perspective view of a side balloon and a side catheter branch of another example catheter assembly.

FIG. 11 is a cross-sectional view taken along line 11-11 of the side balloon and the side catheter branch of FIG. 10.

DETAILED DESCRIPTION

I. Overview

Figure 4:
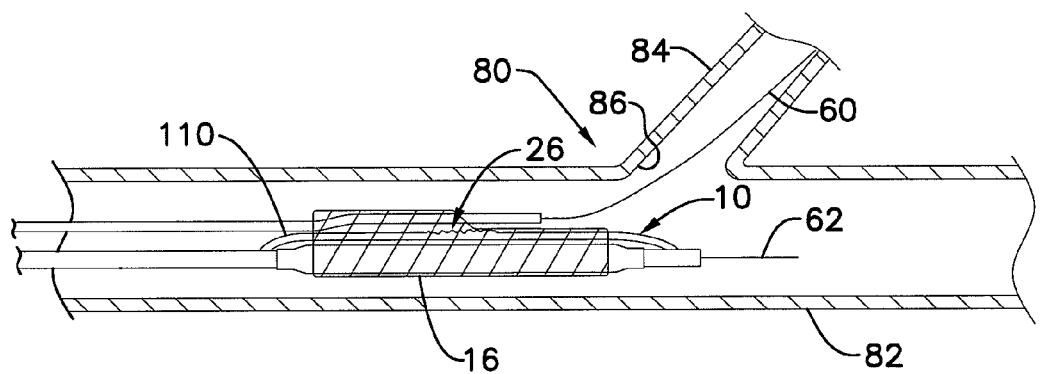
FIG. 4 is a schematic side view of the catheter assembly shown in FIG. 1 in a position prepared for treatment of a vessel bifurcation.

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other; and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively, that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The example catheter assemblies disclosed herein include, at a distal end portion thereof, a main catheter branch and a side catheter branch. The side catheter branch typically includes a side guidewire housing that defines a side guidewire lumen. A distal end portion of the side catheter branch is configured to extend into a branch vessel at a vessel bifurcation. The side catheter branch is used to align features of a stent carried by the proximal end portion of the vessel bifurcation treatment system with an ostium (also referred to as a branch vessel opening) into the branch vessel.

The main catheter branch includes a catheter shaft having a distal end portion. A main balloon and a side balloon are positioned at the distal end portion of the catheter shaft. A main catheter branch includes a main guidewire housing that defines a main guidewire lumen. A distal waist portion of the main balloon is operably mounted to the main guidewire housing. A proximal waist portion of the main balloon is operably mounted to the distal end portion of the catheter shaft.

The side balloon is positioned on a side inflation member that extends generally in parallel with the main balloon. The side inflation member defines a side inflation lumen. The side inflation member includes proximal and distal segments that are connected in fluid communication with the side balloon. The distal and proximal segments of the side inflation member can alternatively be considered elongate waist portions of the side balloon that extend in the distal and proximal directions, respectively.

The waist portion of a balloon is typically at one of the opposing ends of the balloon. The waist portion is used to secure or otherwise mount the balloon to a mounting surface, such as the outer surface of a shaft. Some example mounting surfaces for the waist portions of a main balloon are the outer surface of a distal end portion of a catheter shaft and the outer surface of a main guidewire housing. The waist portion is typically configured to not expand in size when the balloon is inflated with inflation fluid. In many instances a balloon is formed by molding from a length of tubular structure (e.g., a polymeric catheter shaft). The portions of the tubular structure extending on opposite sides of the molded balloon can be considered waist portions of the balloon regardless of the length of the waist portions.

II. The Example Illustrated in FIGS. 1-6

An example catheter assembly 10 is shown schematically with reference to FIGS. 1-3. The catheter assembly 10 is configured for treatment of a vessel bifurcation, such as the vessel bifurcation 80 described below. The catheter assembly 10 includes a main catheter branch 12 and a side catheter branch 14. The main catheter branch 12 includes a catheter shaft 20 having a proximal end portion 28 with a proximal end 18 and a distal end portion 30. The catheter shaft 20 defines a main inflation lumen extending therethrough. The main catheter branch 12 further includes a main guidewire housing 22. The main guidewire housing 22 defines a main guidewire lumen.

The main catheter branch further includes a main balloon 24 extending along the guidewire housing 22. The main balloon 24 includes an inflation portion 43. A proximal waist 38 of the main balloon 24 is operably mounted to the catheter shaft 20, and a distal waist of the main balloon 24 is operably mounted to the main guidewire housing 22.

The main catheter branch 12 further includes a side balloon 26. The side balloon 26 includes an inflatable portion 45, a distal waist 44, and proximal waist 46. The waist members 44, 46 define a side inflation lumen through which inflation fluid is provided to the side balloon 26. When uninflated, the inflatable portion 45 of the side balloon 26 maintains a generally collapsed profile. When inflated as shown in FIG. 2, the inflatable portion 45 of the side balloon 26 extends radially outward relative to the longitudinal axis of the main balloon 24.

Typically, a distal end of the distal waist 44 is operably mounted to the main guidewire member 22 distal of the main balloon 24, and the proximal end of the distal waist 44 is operably mounted in fluid communication with the side balloon 26. A distal end of the proximal waist 46 is operably mounted in fluid communication to the inflation portion 45. A proximal end of the proximal waist 44 is operably mounted to the distal end portion of the catheter shaft 20 in fluid communication with the main inflation lumen therein. The main balloon 24 is also coupled in fluid communication with the inflation lumen. In the arrangement shown in FIG. 2, the inflation portions 43, 45 of the main and side balloons 24, 26 are shown in the inflated states.

The side catheter branch 14 extends generally parallel to the catheter shaft 20. The side catheter branch 14 has a side guidewire lumen 19 (see FIG. 3) extending therethrough. A distal end portion 15 of the side catheter branch 14 is configured to extend into a branch vessel at a vessel bifurcation, as described below. The side catheter branch 14 is used to align features of a stent 16 with the ostium into the branch vessel.

As shown in FIG. 1, the catheter assembly 10 is typically used to deliver the stent 16 to a vessel bifurcation. Once in position at the vessel bifurcation, the main and side balloons 24, 26 are expanded to deploy the stent 16 at the desired location within the vessel bifurcation.

In the arrangement shown, the side catheter branch 14 is connected to the side balloon 26 to orient the side catheter branch 14 relative to the side balloon 26 prior to and after deployment. For example, the side catheter branch 14 is connected or otherwise bonded to the proximal waist 46 of the side balloon 26 at site 110 (also referred to herein as a location 110). As described further below, connecting the side catheter branch 14 to the proximal waist 46 can be helpful to properly orient the side catheter branch 14 during assembly of the catheter assembly. In addition, the connection between the side catheter branch 14 and the proximal waist 46 can also be helpful to maintain the orientation of the side catheter branch 14 with respect to the side balloon 26 upon inflation and deflation of the side balloon 26 during deployment of the stent 16.

The bond at site 110 between the side catheter branch 14 and the proximal waist 46 of the side balloon 26 can be accomplished in a variety of ways. In some examples, the bond at site 110 is created using an adhesive that connects the side catheter branch 14 to the proximal waist 46. Examples of adhesives that can be used to create such a bond include urethane and ultraviolet (UV) curable adhesives. In some examples, heat can be used to form the connection between, for example, a side branch catheter and a waist that are formed of thermoplastic materials. In yet other arrangements, the bond at site 110 is created by coextrusion of the side catheter branch 14 and the proximal waist 46 of the side balloon 26. In yet other examples, the bond is created by smart bonding using radio frequency (RF), or by welding the side catheter branch 14 to the side balloon 26 at the site 110. For example, a through transmission layer welding (TTLW) technique can be used to weld the side catheter branch 14 to the side balloon 26 at the site 110.

As shown in FIG. 3, in some arrangements, the outer surface of the side catheter branch 14 forms a generally crescent or U-shaped section 120 sized to receive a portion of the proximal waist 46 to which the side catheter branch 14 is attached. The section 120 helps to locate the side catheter branch 14 relative to the proximal waist 46 during attachment, as well as provides a greater surface area for the bond between the proximal water 46 and the side catheter branch 14 at the site 110. In addition, the section 120 can allow for a lower profile for the side catheter branch 14 at the site 110. The section 120 can have other shapes in addition to or in place of the crescent or U-shape illustrated.

In some examples, sides 122, 124 of the section 120 are formed at slopes of about 45 to about 60 degrees relative to the normal axis of the side catheter branch 14. In some examples, an entire length of the side catheter branch 14 includes the section 120. In other embodiments, only a mid-portion of the side catheter branch 14 adjacent to the site 110 includes the section 120. In other embodiments, the crescent or U-shaped section 120 can be formed in the waist 46, rather than the side branch catheter 14. Other configurations are possible.

Figure 5:
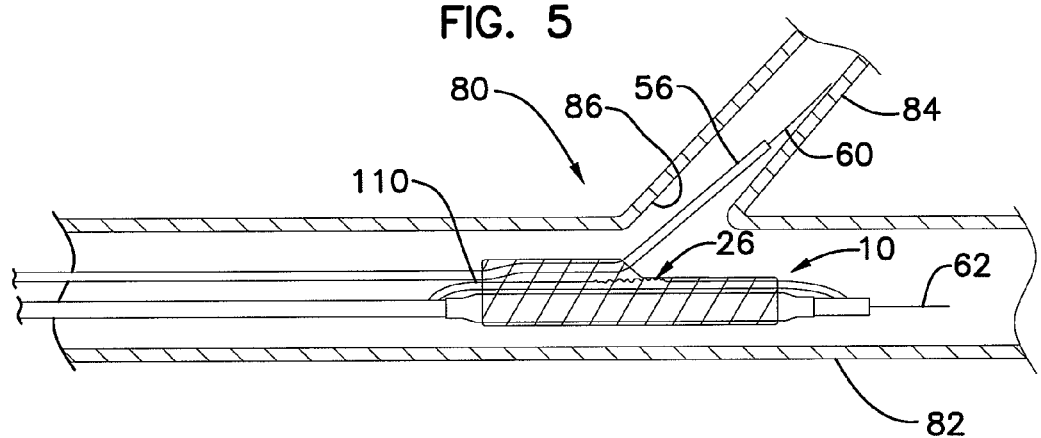
FIG. 5 is a schematic side view of the catheter assembly shown in FIG. 4 with the side catheter branch extending into a branch vessel of the vessel bifurcation.
Figure 6:
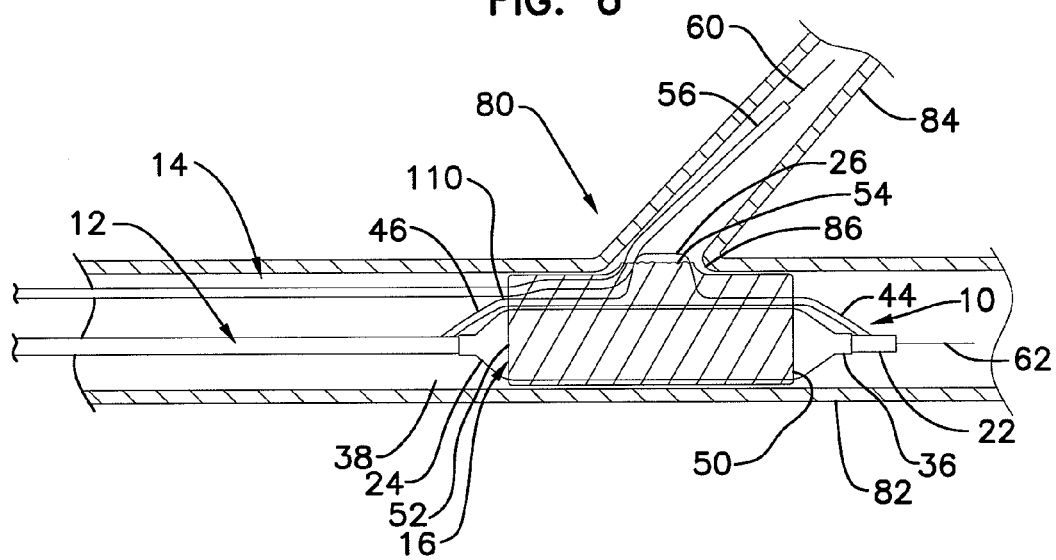
FIG. 6 is a schematic side view of the catheter assembly shown in FIG. 5 with the side and main balloons inflated and the stent expanded at the vessel bifurcation.

Referring now to FIGS. 4-6, the catheter assembly 10 can be used for treatment of a vessel bifurcation 80. Typically, a main vessel guidewire 62 is inserted into a main vessel 82 of the vessel bifurcation 80 to a point distal of the vessel bifurcation. A branch vessel guidewire 60 is advanced to the vessel bifurcation and inserted through an ostium or opening 86 of a branch vessel 84. A proximal end of the main vessel guidewire 62 is then inserted into the main guidewire lumen 34, and a proximal end of the branch vessel guidewire 60 is inserted into a branch guidewire lumen defined by the side catheter branch 14. The catheter assembly 10 is advanced over the guidewires 60, 62 to the vessel bifurcation. The catheter assembly 10 is then advanced further distally until the distal end portion 56 of the side catheter branch 14 is positioned within the branch vessel 60. A marker system (described further below) can be used to help confirm proper radial and axial alignment of the lateral branch opening 54 of the stent 16 relative to the ostium 86 into the branch vessel 84.

After proper positioning of the catheter assembly 10 is confirmed, the main and branch balloons 24, 26 are inflated. Typically, inflation of the side balloon 26 can also result in expansion of expandable structure 55 surrounding the lateral branch opening 54. The expanded expandable structure 55 can extend through the ostium 86 and at least partially into the branch vessel 84. Since the side catheter branch 14 is connected to the proximal waist 14 at site 110, the side catheter branch 14 remains oriented with the side balloon 26 during the inflation and subsequent deflation of the side balloon 26.

In some arrangements, connection of the side catheter branch 14 to the side balloon 26 allows the distal waist 44 of the side balloon 26 to be truncated. In this manner, the distal waist 44 need not be attached to the main guidewire housing 22 at the distal end of the catheter assembly 10 to maintain the orientation of the side balloon 26.

There are one or more advantages associated with connecting the side catheter branch to the side balloon. For example, by connecting the side catheter branch to the side balloon, the side catheter branch remains oriented with respect to the side balloon during assembly of the catheter assembly. For example, the side catheter branch remains centered on the side balloon as the stent is crimped over the side catheter branch and the side balloon during assembly.

In another example, the side catheter branch remains oriented with respect to the side balloon after inflation thereof, deployment of the stent, and deflation of the side balloon. Because the side balloon remains oriented with respect to the side catheter branch, the side balloon also remains oriented with respect to the ostium and the expandable structure of the stent. In this manner, it is possible to reinflate the side balloon, if necessary, to aid in the further expansion of the expandable structure within the ostium. This is possible because the side catheter branch remains oriented with respect to the side balloon even after deflation of the side balloon.

III. The Example Illustrated in FIG. 7

Referring now to FIG. 7, a distal portion 200 of another example catheter assembly is shown. The distal portion 200 includes the main balloon 24 with a bulge portion 226 located on the main balloon 24 between the proximal and distal waists 38, 36. The bulge portion 226 can be positioned to expand the expandable structure 55 surrounding the lateral branch opening 54 of the stent 16, similarly to the side balloon 26 described above.

The side catheter branch 14 is connected to the main balloon 24 at a site 210 adjacent to the proximal waist 38 of the main balloon 24. In addition, the side catheter branch 14 can be connected to the bulge portion 226 at a site 220. In this manner, the side branch catheter 14 maintains its orientation relative to the main balloon 24 prior to and after inflation of the main balloon during delivery of a stent (not shown).

In other arrangements, the side catheter branch can be connected to other portions of the catheter assembly. For example, in one alternative arrangement, the side catheter branch 14 is connected at multiple sites to the main balloon 24. In yet another arrangement, the side catheter branch 14 is connected to the waist 38 of the main balloon 24 at one or more sites. In yet a further example, the side catheter branch 14 is connected to the bulge 226 at multiple sites. In other arrangements, the side catheter branch 14 is connected to the main catheter branch 12 and/or the main or side balloons 24, 26 at one or more sites. Other configurations are possible.

IV. The Example Illustrated in FIGS. 8 and 9

Referring now to FIGS. 8 and 9, a distal portion 300 of another example catheter assembly is shown. A side balloon 326 of the distal portion 300 includes a channel 310 formed therein that is sized to receive a portion of the side catheter branch 14. In the arrangement shown, the channel 310 is formed in a proximal side 330 of the inflation portion 345 of the side balloon 326 and extends from a first end 332 adjacent to the proximal waist 46 to a second end 334.

In example arrangements, the channel 310 is formed of sufficient depth to receive at least a portion of the side catheter branch 14 therein. In one example, the depth of the channel 310 is in the range of about 0.1 to about 2 mm. In some arrangements, the side catheter branch 14 can be bonded to the channel 310 using one or more of the techniques described above. In one example, the side catheter branch 14 is connected to the channel 310 at a single site within the channel 310. In another example, the side catheter branch 14 is connected to the channel 310 at multiple sites within the channel 310. In yet another embodiment, the side catheter branch 14 is connected to the channel 310 along substantially an entire length of that portion of the side catheter branch 14 that is positioned within the channel 310. In some embodiments, the side catheter branch 14 can also be connected to the proximal waist 46 of the side balloon 326, as described above.

In another example, the side catheter branch 14 can simply be placed in the channel 310 during assembly of the distal portion 300 of the catheter assembly, and the depth of the channel 310 can maintain the side catheter branch 14 in the channel 310 prior to and after deployment of the side balloon 326.

In example arrangements, the channel 310 is formed in the side balloon 326 during assembly of the balloon 326. For example, the channel 310 can be formed using a crescent-shaped mold that is used to mold the channel 310 into the side balloon 326 during assembly. In yet another example, the side balloon 326 includes a thermoplastic polymer material, and the channel 310 can be formed by ablating a portion of the side balloon 326 using, for example, a laser ablation technique. Other configurations are possible.

V. The Example Illustrated in FIGS. 10 and 11

Referring now to FIGS. 10 and 11, a distal portion 400 of another example catheter assembly is shown. A side balloon 426 of the distal portion 400 is shown in a deflated state, including adjacent balloon peaks 410, 412. Balloon peaks 410, 412 are typically folded over one another during assembly to form a low catheter profile.

In the arrangement shown, the side catheter branch 14 is positioned to extend in a channel 216 between the balloon peaks 410, 412. In one example, the balloon peaks 410, 412 can then be folded over the side catheter branch 14, and the stent can then be crimped around the side balloon 426 to maintain the side balloon 426 and the side catheter branch 14 in place during delivery to a vessel treatment site.

In some examples, the side balloon 426 can be formed so that the side balloon 426 maintains the shape of the channel 416 when the side balloon 426 is inflated, similar to the shape of channel 310 described above. In this manner, the side catheter branch 14 remains oriented with respect to the side balloon 426 after inflation of the side balloon 426. In one alternative arrangement, the side catheter branch 14 can be positioned within the balloon peaks of the main balloon, rather than the side balloon.

It can be advantageous to position the side catheter branch in the channel between balloon peaks to allow the side catheter branch to remain oriented with respect to the side balloon during assembly of the catheter assembly. For example, the side catheter branch can be positioned between balloon peaks during folding of the balloon. The stent can then be crimped onto the balloon, and the side catheter branch remains centered on the balloon during the crimping process. In addition, the side catheter branch can remain oriented with respect to the side balloon during inflation of the side balloon during expansion of the stent.

VI. Alternative Materials and Arrangements

In some arrangements, the catheter assembly 10 and distal portions 200, 300, 400 can include marker material that is visible under X-ray or in fluoroscopy procedures. In some examples, the mark material is positioned along the distal end portions of the main and side catheter branches. Any features of the system 10 that include marker material can be more easily identified and distinguished under X-ray or in fluoroscopy procedures. Some example marker materials include gold, platinum and tungsten. In one embodiment, the marker material can be included in a band structure that is secured to at least one of the main and side catheter branches 12, 14. In other embodiments, the marker material is part of the material composition of portions of the main and side catheter branches 12, 14. Viewability of features of the catheter assembly 10 under X-ray or fluoroscopy can assist the physician operating the system 10 to more easily adjust a position of the system 10 relative to the vessel bifurcation 80. Example markers and marker materials suitable for use with system 10 are described in U.S. Pat. No. 6,692,483 and U.S. Pat. Publ. No. 2007/0203512, which patent matters are incorporated herein by reference.

In some examples, at least one marker is positioned at the site at which the side catheter branch is connected to the side or main balloons (e.g., sites 110, 210, 220). In this manner, the site of the connection of the side catheter branch to the balloon can be readily identified during deployment of the catheter assembly.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429, 6,325,826, 6,706,062, and 7,220,275, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX®

(available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

VII. Conclusion

One aspect of the present disclosure relates to a catheter assembly for deployment in a bifurcated vessel. The catheter assembly includes a catheter shaft, a balloon, and a side catheter branch. The catheter shaft extends from a proximal end portion to a distal end portion. The balloon includes a proximal waist and an exterior surface, wherein the proximal waist is operatively coupled to the distal end portion of the catheter shaft. The side catheter branch extends generally parallel to the distal end portion of the catheter shaft. The side catheter branch is connected to the balloon at a location on the exterior surface of the balloon.

Another aspect of the present disclosure relates to a catheter assembly for deployment in a bifurcated vessel. The catheter assembly includes a catheter shaft, a balloon, and a side catheter branch. The catheter shaft extends from a proximal end portion to a distal end portion. The balloon includes a proximal waist operatively coupled to the distal end portion of the catheter shaft, wherein the balloon defines a plurality of balloon peaks prior to inflation of the balloon. The side catheter branch extends generally parallel to the distal end portion of the catheter shaft. The side catheter branch extends between the balloon peaks prior to a stent being crimped around the balloon and the side catheter branch.

A further aspect of the present disclosure relates to a method for forming a catheter assembly for deployment in a bifurcated vessel. The catheter assembly includes a catheter shaft extending from a proximal end portion to a distal end portion, a balloon having a proximal waist and an outer surface, and a side catheter branch. The method includes coupling the proximal waist of the balloon to the distal end portion of the catheter shaft, and connecting a side catheter branch to an outer surface of the balloon at a connection location, the side catheter branch extending generally parallel to the distal end portion of the catheter shaft.

It is noted that not all of the features characterized herein need to be incorporated within a given arrangement, for the arrangement to include improvements according to the present disclosure.

What is claimed is:

1. A catheter assembly for deployment in a bifurcated vessel, the assembly comprising:
   (a) a catheter shaft including proximal and a distal portion;
   a balloon including a proximal waist, a distal waist and an inflatable portion extending therebetween, and an exterior surface the proximal waist being directly connected to the distal portion of the catheter shaft and the distal waist being directly connected to the distal portion of the catheter shaft; and
   a side catheter branch extending generally parallel to the distal portion of the catheter shaft, the side catheter branch defining a U-shaped portion that is bonded to the exterior surface of the balloon at a location proximal of the inflatable portion, wherein a distal end of the side catheter branch is configured to extend into a branch Vessel of the bifurcated vessel.

2. The catheter assembly of claim 1, wherein the location is at the proximal waist of the balloon.

3. The catheter assembly of claim 2, wherein the side catheter branch is connected to an inflation portion of the balloon at a second location that is positioned distal of the proximal waist.

4. The catheter assembly of claim 1, wherein the location is at an inflation portion of the balloon located distal of the proximal waist.

5. The catheter assembly of claim 1, wherein the balloon is a side balloon, and wherein the catheter assembly further comprises a main balloon including a main proximal waist connected to the distal end portion of the catheter shaft.

6. The catheter assembly of claim 1, wherein the balloon defines a channel sized to receive the side catheter branch.

7. A method for forming a catheter assembly for deployment in a bifurcated vessel, the catheter assembly including a catheter shaft extending from a proximal end portion to a distal end portion, a first inflatable portion, a second inflatable portion, and a side catheter branch, the second inflatable portion configured to extend radially outward from the first inflatable portion, the method comprising:
   coupling a proximal waist of the first inflatable portion to the distal end portion of the catheter shaft;
   coupling a distal waist of the first inflatable portion to the distal end portion of the catheter shaft;
   forming a U-shaped in an outer surface of the side catheter branch;
   positioning the U-shaped section over the proximal waist of the first inflatable portion; and
   bonding the side catheter branch to an exterior surface of the second inflatable portion at a first connection location and bonding the U-shaped section of the side catheter branch to the proximal waist of the first inflatable portion at a second connection location, the side catheter branch extending generally parallel to the distal end portion of the catheter shaft and configured to extend into a branch vessel of the bifurcated vessel.

8. The method of claim 7, wherein bonding the side catheter branch further comprises bonding the side catheter branch at multiple connection locations along a length of the first inflatable portion, a length of the second inflatable portion, or both.

9. The method of claim 7, further comprising forming a channel in the second inflation portion, of the channel being sized to receive at least a portion of the side catheter branch.

10. The method of claim 9, wherein bonding the side catheter branch further comprising connecting the side catheter branch to the second inflatable portion at multiple locations along the channel.

11. The method of claim 7, wherein the second inflatable portion includes a second proximal waist and a second distal waist, and wherein the method further comprises connecting the second proximal waist to the distal end portion of the catheter shaft and the second distal waist to the distal end portion of the catheter shaft.

12. The method of claim 7, wherein the second inflatable portion is a protrusion formed on the first inflatable portion.

13. A catheter assembly for deployment in a bifurcated vessel, the bifurcated vessel including a main vessel and a branch vessel, the assembly comprising:
   a catheter shaft including a proximal region and a distal region, the catheter shaft defining a main guidewire lumen, the catheter shaft configured to extend through the main vessel of the bifurcated vessel;
   a main balloon disposed about at least a portion of the distal region of the catheter shaft;
   a side balloon including a side proximal waist and a side distal waist, the side proximal waist being connected to the distal region of the catheter shaft and the side distal waist being connected to the distal region of the catheter shaft; and a side catheter branch extending adjacent to at least the distal region of the catheter shaft and defining a secondary guidewire lumen, the side catheter branch defining a U-shaped portion that contacts the side balloon at a location on the exterior surface of the side balloon, wherein the side catheter branch is bonded to the exterior surface of the side balloon at the location, the side catheter branch configured to extend into the branch vessel.

14. The catheter assembly of claim 13, wherein the side branch is bonded to the exterior surface of the side balloon at the side proximal waist.

15. The catheter assembly of claim 13, wherein the side branch is bonded to the exterior surface of the side balloon distal of the side proximal waist.

16. The catheter assembly of claim 13, wherein the side branch is bonded to the exterior surface of the side balloon at a plurality of locations.

17. The catheter assembly of claim 13, wherein the side proximal waist is connected to the distal region of the catheter shaft adjacent to a main proximal waist of the main balloon, and the side distal waist is connected to the distal region of the catheter shaft adjacent to a main distal waist of the main balloon.

* * * * *